(12) United States Patent
Hattangadi et al.

(10) Patent No.: US 8,603,064 B2
(45) Date of Patent: Dec. 10, 2013

(54) DOUBLE BALLOON CATHETER AND METHODS FOR HOMOGENEOUS DRUG DELIVERY USING THE SAME

(75) Inventors: Neil Hattangadi, Plymouth, MN (US); Daniel Lerner, Plymouth, MN (US); Ryan Olivera, Plymouth, MN (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 13/446,400

(22) Filed: Apr. 13, 2012

(65) Prior Publication Data

US 2012/0259315 A1    Oct. 11, 2012

Related U.S. Application Data

(62) Division of application No. 12/564,771, filed on Sep. 22, 2009, now Pat. No. 8,162,879.

(60) Provisional application No. 61/099,127, filed on Sep. 22, 2008.

(51) Int. Cl.
*A61M 31/00* (2006.01)

(52) U.S. Cl.
USPC .............. 604/509; 604/101.01; 604/101.03; 604/101.04; 604/101.05; 604/102.02

(58) Field of Classification Search
USPC ............ 604/96.01, 100.01, 101.01, 101.03, 604/101.04, 101.05, 102.01, 102.02, 604/102.03, 103.1, 506, 507, 508, 509
See application file for complete search history.

(56) References Cited

U.S. PATENT DOCUMENTS

| | | | |
|---|---|---|---|
| 4,610,662 A | 9/1986 | Weikl et al. | |
| 4,696,668 A | 9/1987 | Wilcox et al. | |
| 4,714,460 A | 12/1987 | Calderon | |
| 4,781,667 A | 11/1988 | Kitai | |
| 4,824,436 A | 4/1989 | Wolinsky | |
| 4,867,742 A | 9/1989 | Calderon | |
| 4,883,459 A | 11/1989 | Calderon | |
| 4,921,478 A | 5/1990 | Solano et al. | |
| 4,976,692 A | 12/1990 | Atad | |
| 5,059,178 A | 10/1991 | Ya | |

(Continued)

FOREIGN PATENT DOCUMENTS

| CA | 2232277 A1 | 10/1998 |
|---|---|---|
| CH | 671883 A5 | 10/1989 |

(Continued)

OTHER PUBLICATIONS

US 6,348,062, 02/2002, Hopkins (withdrawn)

*Primary Examiner* — Bhisma Mehta
(74) *Attorney, Agent, or Firm* — Alana T. Bergman, Esq.

(57) ABSTRACT

The present disclosure is directed to a catheter for site-specific delivery of a therapeutic agent to a blood vessel of a patient. The catheter further includes an elongated shaft having at least one inner lumen, a distal end and a proximal end and proximal and distal vessel-conforming balloons where each is separately positionable and inflatable, and when inflated, substantially restricts blood flow in the vessel and creates a treatment window of a defined but variable length for delivery of the therapeutic agent. The catheter optionally includes at least one marker band adjacent to the proximal balloon and at least one marker band adjacent to the distal balloon. At least one lateral aperture positioned in the window is in fluid communication with a drug delivery conduit located within either the inner shaft or the outer shaft to provide a homogeneous concentration of the therapeutic agent to the window.

17 Claims, 11 Drawing Sheets

(56) References Cited

U.S. PATENT DOCUMENTS

| | | |
|---|---|---|
| 5,129,883 A | 7/1992 | Black |
| 5,152,277 A | 10/1992 | Honda et al. |
| 5,163,906 A | 11/1992 | Ahmadi |
| 5,320,604 A | 6/1994 | Walker et al. |
| 5,380,284 A | 1/1995 | Don Michael |
| 5,397,307 A | 3/1995 | Goodin |
| 5,411,479 A | 5/1995 | Bodden |
| 5,415,636 A | 5/1995 | Forman |
| 5,419,763 A | 5/1995 | Hildebrand |
| 5,505,701 A | 4/1996 | Fernandez de Lomana |
| 5,514,092 A | 5/1996 | Forman et al. |
| 5,527,292 A | 6/1996 | Adams et al. |
| 5,554,119 A | 9/1996 | Harrison et al. |
| 5,558,642 A | 9/1996 | Schweich, Jr. et al. |
| 5,662,609 A | 9/1997 | Slepian |
| 5,779,673 A | 7/1998 | Roth et al. |
| 5,833,650 A | 11/1998 | Imran |
| 5,836,967 A | 11/1998 | Schneider |
| 5,908,407 A | 6/1999 | Frazee et al. |
| 5,919,163 A | 7/1999 | Glickman |
| 5,947,977 A | 9/1999 | Slepian et al. |
| 6,086,527 A | 7/2000 | Talpade |
| 6,206,868 B1 | 3/2001 | Parodi |
| 6,295,989 B1 | 10/2001 | Connors, III |
| 6,299,599 B1 | 10/2001 | Pham et al. |
| 6,312,444 B1 | 11/2001 | Barbut |
| 6,363,900 B1 | 4/2002 | Homi et al. |
| 6,371,971 B1 | 4/2002 | Tsugita et al. |
| 6,383,205 B1 | 5/2002 | Samson et al. |
| 6,413,235 B1 | 7/2002 | Parodi |
| 6,485,500 B1 | 11/2002 | Kokish et al. |
| 6,488,672 B1 | 12/2002 | Dance et al. |
| 6,537,195 B2 | 3/2003 | Forman |
| 6,605,030 B2 | 8/2003 | Weinberger |
| 6,623,452 B2 | 9/2003 | Chien et al. |
| 6,626,885 B2 | 9/2003 | Massengale |
| 6,632,196 B1 | 10/2003 | Houser |
| 6,673,040 B1 | 1/2004 | Samson et al. |
| 6,685,672 B1 | 2/2004 | Forman |
| 6,692,458 B2 | 2/2004 | Forman et al. |
| 6,726,674 B2 | 4/2004 | Leu |
| 6,790,196 B2 | 9/2004 | Kokate et al. |
| 6,997,898 B2 | 2/2006 | Forman |
| 7,060,051 B2 | 6/2006 | Palasis |
| 7,066,905 B2 | 6/2006 | Squire et al. |
| 7,122,019 B1 | 10/2006 | Kesten et al. |
| 7,131,963 B1 | 11/2006 | Hyde |
| 7,229,462 B2 | 6/2007 | Sutton et al. |
| 7,329,237 B2 | 2/2008 | Yokoyama et al. |
| 7,338,467 B2 | 3/2008 | Lutter |
| 7,374,561 B2 | 5/2008 | Barbut |
| 2001/0031982 A1 | 10/2001 | Peterson et al. |
| 2001/0039411 A1 | 11/2001 | Johansson et al. |
| 2001/0044598 A1 | 11/2001 | Parodi |
| 2001/0047184 A1 | 11/2001 | Connors |
| 2001/0049517 A1 | 12/2001 | Zadno-Azizi et al. |
| 2002/0016564 A1 | 2/2002 | Courtney et al. |
| 2002/0016565 A1 | 2/2002 | Zadno-Azizi |
| 2002/0029031 A1 | 3/2002 | Bagaoisan et al. |
| 2002/0052638 A1 | 5/2002 | Zadno-Azizi |
| 2002/0077594 A1 | 6/2002 | Chien et al. |
| 2002/0121472 A1 | 9/2002 | Garner et al. |
| 2002/0123765 A1 | 9/2002 | Sepetka et al. |
| 2002/0165574 A1 | 11/2002 | Ressemann et al. |
| 2002/0165598 A1 | 11/2002 | Wahr et al. |
| 2002/0188253 A1 | 12/2002 | Gordon et al. |
| 2003/0120208 A1 | 6/2003 | Houser et al. |
| 2004/0092870 A1 | 5/2004 | Squire et al. |
| 2005/0159703 A1 | 7/2005 | Yokoyama et al. |
| 2005/0245893 A1 | 11/2005 | Leschinsky |
| 2005/0288632 A1* | 12/2005 | Willard .................. 604/103.01 |
| 2006/0106338 A1 | 5/2006 | Chang |
| 2006/0129095 A1 | 6/2006 | Pinchuk |
| 2006/0200083 A1 | 9/2006 | Freyman et al. |
| 2007/0010782 A1 | 1/2007 | Doty et al. |
| 2007/0088256 A1 | 4/2007 | Intoccia |
| 2008/0086083 A1 | 4/2008 | Towler |
| 2008/0114286 A1 | 5/2008 | Hamel et al. |

FOREIGN PATENT DOCUMENTS

| | | |
|---|---|---|
| DE | 32 27 575 A1 | 2/1984 |
| DE | 40 01 086 A1 | 7/1991 |
| DE | 40 09 468 A1 | 9/1991 |
| DE | 44 21 920 A1 | 1/1995 |
| DE | 19 526 784 A1 | 1/1997 |
| DE | 19 900 698 A1 | 7/2000 |
| DE | 19 911 942 A1 | 9/2000 |
| DE | 10 036 164 A1 | 2/2002 |
| EP | 0 427 429 A2 | 5/1991 |
| EP | 0 474 906 A1 | 3/1992 |
| EP | 0 707 864 A1 | 4/1996 |
| EP | 0 774 991 B1 | 5/1997 |
| EP | 0 839 550 A1 | 5/1998 |
| EP | 0 872 257 A2 | 10/1998 |
| EP | 1 669 099 A1 | 6/2006 |
| FR | 2 803 532 A1 | 7/2001 |
| JP | 54-31985 A | 3/1979 |
| JP | 10-015063 A | 1/1989 |
| JP | 10-027564 A | 1/1989 |
| JP | 2-107274 A | 4/1990 |
| JP | 2-255155 A | 10/1990 |
| JP | 3-039170 A | 2/1991 |
| JP | 4-132562 A | 5/1992 |
| JP | 5-042224 A | 2/1993 |
| JP | 6-030998 A | 2/1994 |
| JP | 6-218048 A | 8/1994 |
| JP | 10-155909 A | 6/1998 |
| JP | 10-179750 A | 7/1998 |
| JP | 11-033120 A | 2/1999 |
| JP | 11-164890 A | 6/1999 |
| JP | 11-164891 A | 6/1999 |
| JP | 11-319103 A | 11/1999 |
| JP | 11-319109 A | 11/1999 |
| JP | 2003-250896 A | 9/2003 |
| WO | WO 85/01212 A1 | 3/1985 |
| WO | WO 86/05990 A1 | 10/1986 |
| WO | WO 87/07510 A1 | 12/1987 |
| WO | WO 88/03389 A1 | 5/1988 |
| WO | WO 90/07352 A1 | 7/1990 |
| WO | WO 94/28963 A1 | 12/1994 |
| WO | WO 95/05209 A1 | 2/1995 |
| WO | WO 95/05210 A1 | 2/1995 |
| WO | WO 95/11719 A1 | 5/1995 |
| WO | WO 95/15782 A1 | 6/1995 |
| WO | WO 97/36630 A1 | 10/1997 |
| WO | WO 98/46309 A1 | 10/1998 |
| WO | WO 99/08744 A1 | 2/1999 |
| WO | WO 99/11316 A1 | 3/1999 |
| WO | WO 99/45835 A2 | 9/1999 |
| WO | WO 00/32266 A1 | 6/2000 |
| WO | WO 00/56391 A1 | 9/2000 |
| WO | WO 00/76390 A2 | 12/2000 |
| WO | WO 01/05462 A1 | 1/2001 |
| WO | WO 01/08743 A1 | 2/2001 |
| WO | WO 01/10343 A1 | 2/2001 |
| WO | WO 01/19445 A1 | 3/2001 |
| WO | WO 01/70325 A2 | 9/2001 |
| WO | WO 01/70326 A1 | 9/2001 |
| WO | WO 02/11627 A2 | 2/2002 |
| WO | WO 02/055130 A2 | 7/2002 |
| WO | WO 02/087677 A2 | 11/2002 |
| WO | WO 03/086525 A1 | 10/2003 |
| WO | WO 2004/045702 A1 | 6/2004 |
| WO | WO 2004/069289 A2 | 8/2004 |
| WO | WO 2006/048883 A1 | 5/2006 |
| WO | WO 2006/062653 A1 | 6/2006 |
| WO | WO 2006/093273 A1 | 9/2006 |
| WO | WO 2007/001701 A1 | 1/2007 |
| WO | WO 2007/075311 A1 | 7/2007 |
| WO | WO 2007/100365 A1 | 9/2007 |

* cited by examiner

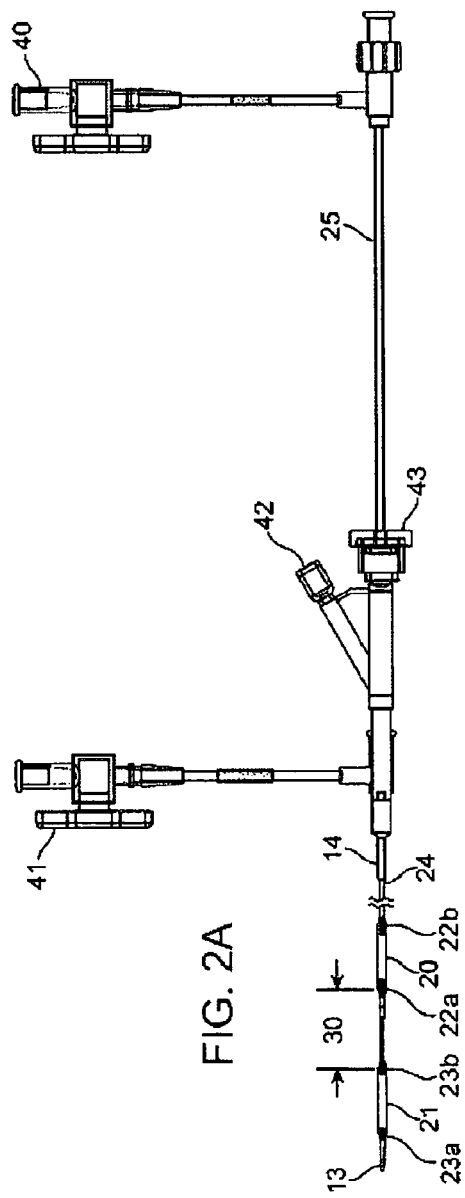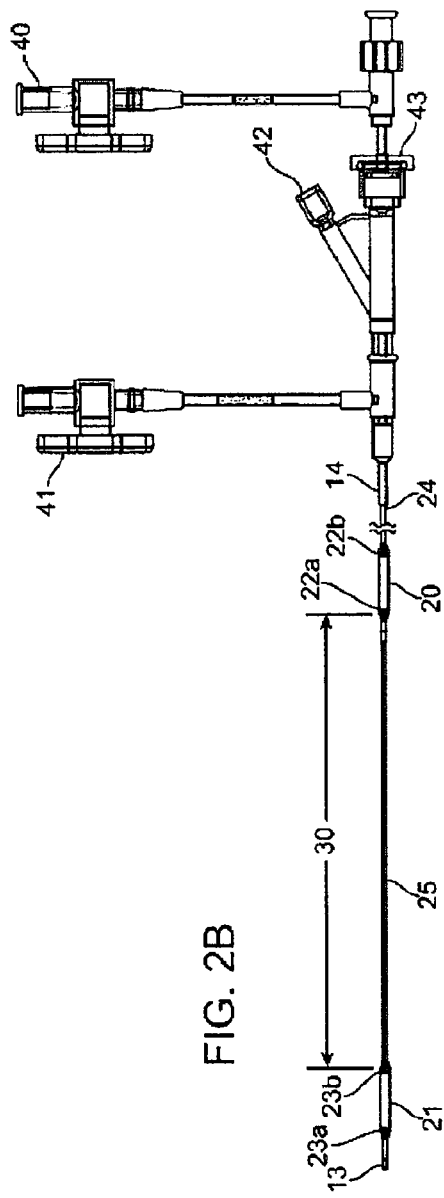
FIG. 2A
FIG. 2B

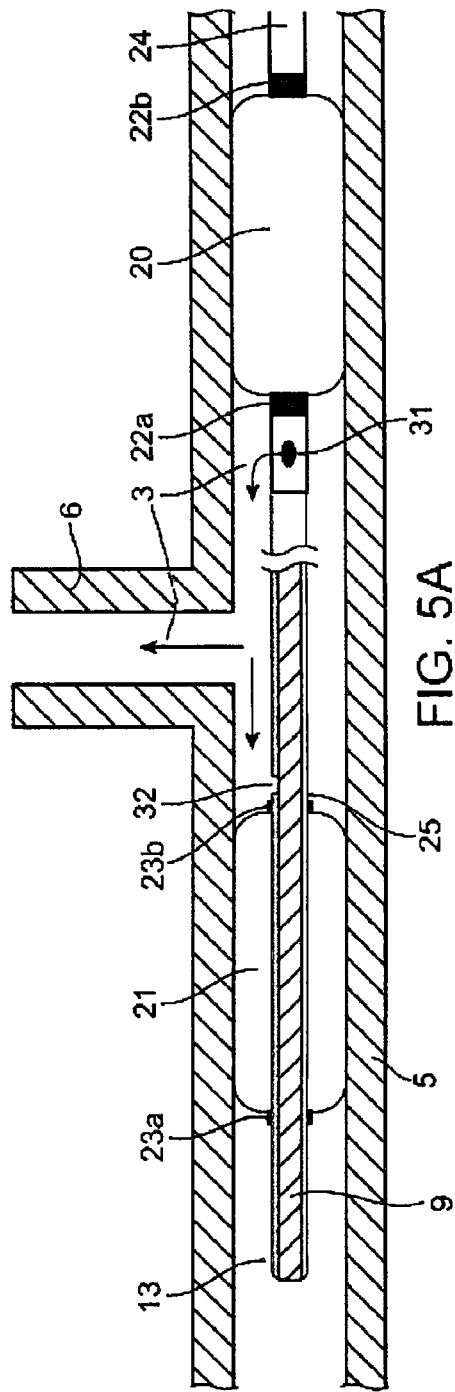
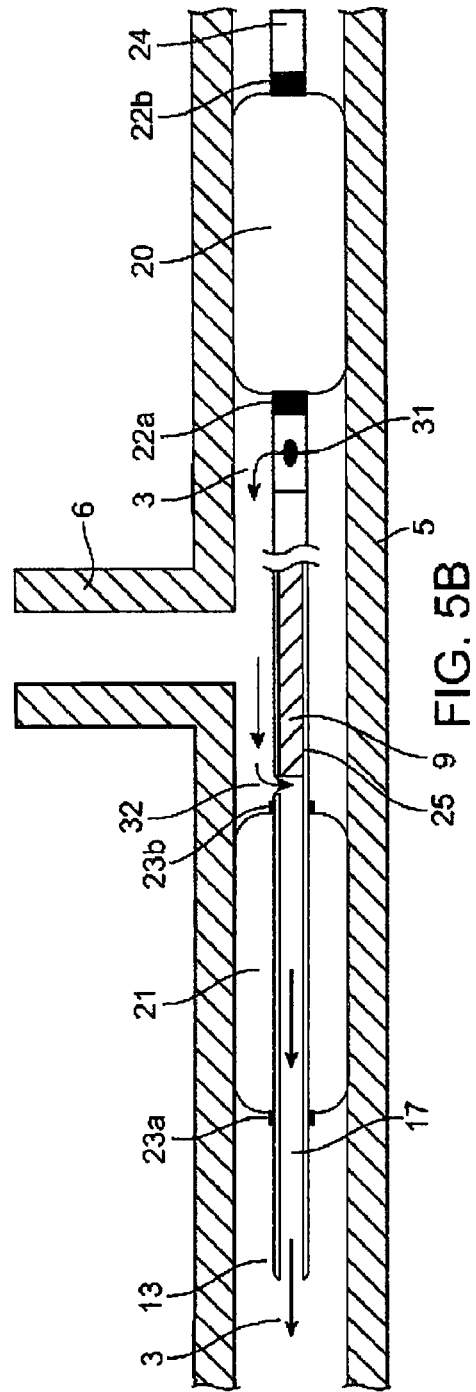
FIG. 5A
FIG. 5B

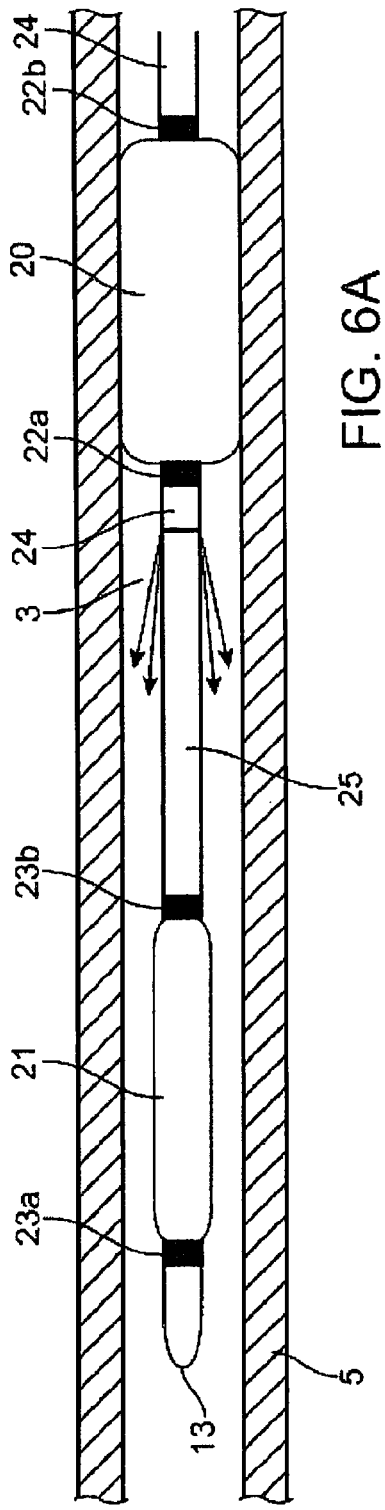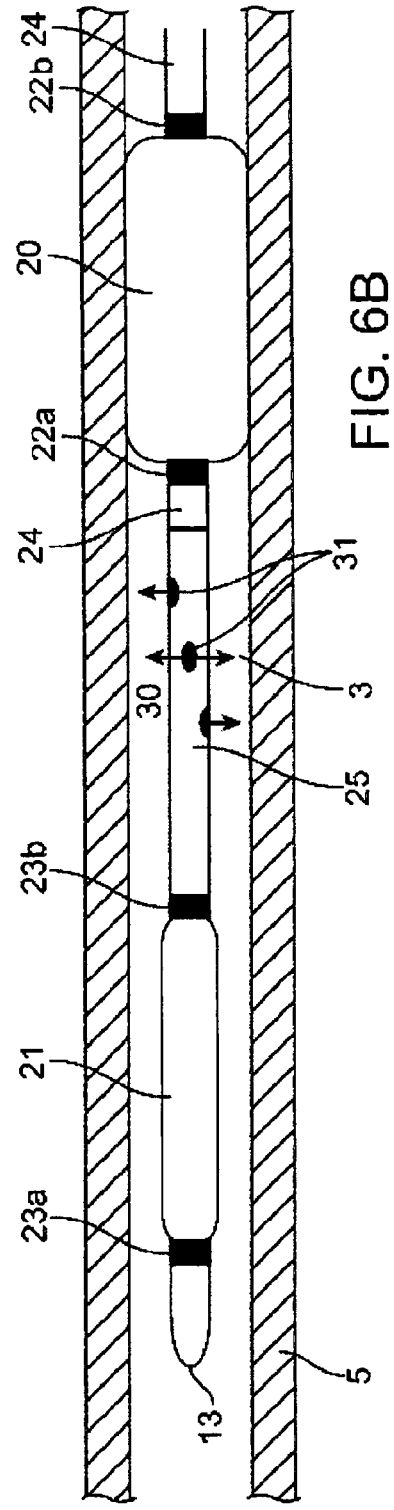

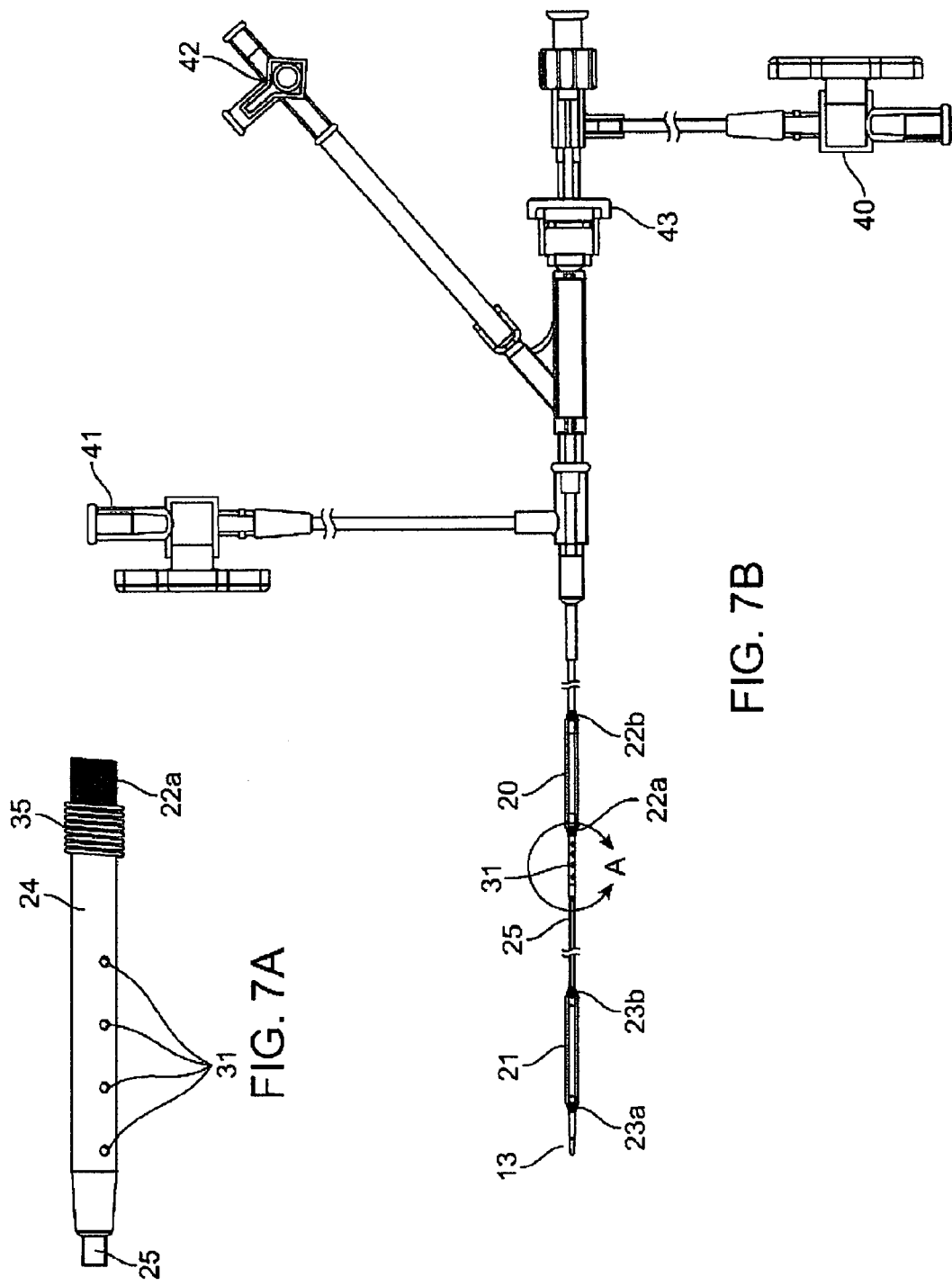

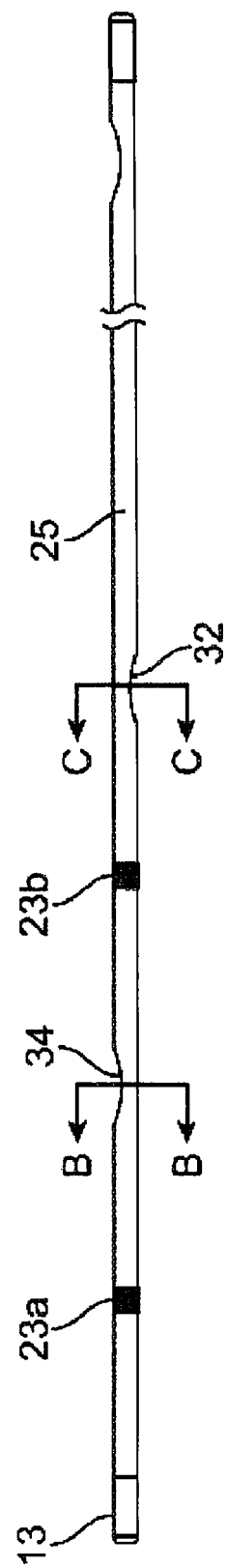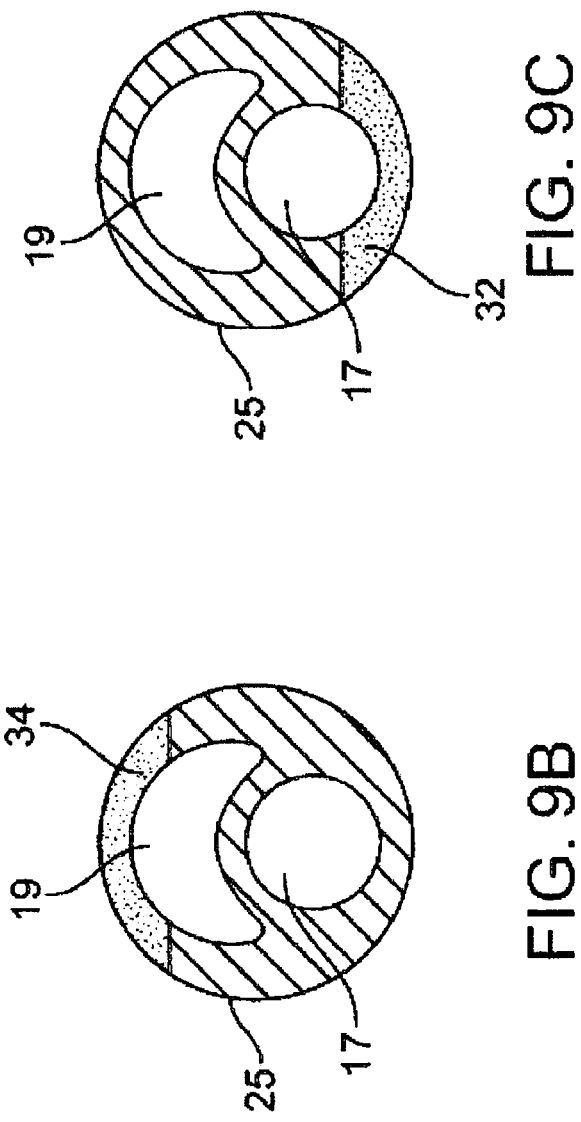
FIG. 9A
FIG. 9B
FIG. 9C

DOUBLE BALLOON CATHETER AND METHODS FOR HOMOGENEOUS DRUG DELIVERY USING THE SAME

CROSS REFERENCE TO RELATED APPLICATIONS

This Application is a divisional of U.S. patent application Ser. No. 12/564,771, filed Sep. 22, 2009, now U.S. Pat. No. 8,162,879, which claims the benefit under 35 U.S.C. §119(e) of provisional application Ser. No. 61/099,127 filed Sep. 22, 2008, the entire contents of which are incorporated herein by this reference.

TECHNICAL FIELD

This present disclosure relates to a double balloon catheter and a method for the site-specific delivery of a therapeutic agent to a blood vessel.

BACKGROUND OF THE RELATED ART

It is often desirable to deliver therapeutic agents into the vascular system of a patient's body to treat medical conditions, such as stenosis and other diseases of the vessel, and to prevent the reoccurrence of these conditions; however, the site-specific delivery of these agents presents many challenges. Known methods for treating stenosis and other diseases of the vessel include the delivery of anti-proliferative agents, anti-inflammatory agents, and thrombolytics by infusing the agents into the blood vessels using an infusion catheter. In addition, infusion catheters have been equipped with a porous perfusion balloon, electrode and/or heating elements on or in the balloon to cause electroporation or to heat the surrounding tissue to improve drug delivery. However, infusion catheters equipped as described have many potential problems, including too large a dose is required (which causes systemic toxicity), too long an exposure time is required, and direct vessel injury can occur from electrodes, heating elements, etc.

In an effort to avoid some of the problems with infusion delivery, the therapeutic agent can be delivered to the vascular site by leaching or extravascular methods. The therapeutic agent can be embedded in or deposited on a catheter, on the wall of a non-porous balloon or in a coating on the catheter or a stent. These methods can prevent the formation of plaques and/or narrowing of the vessel. However, the coating can chip off during delivery and migrate to undesired locations. In addition, a major drawback of a coating is that continued leaching prevents proper vessel healing, leading to thrombosis. Extravascular methods such as injecting therapeutic agents directly into a desired tissue region or attaching a polymer gel or drug-soaked sponge to the outside of a vessel are known. The injection of therapeutic agents would likely result in the contact of the therapeutic agent with healthy tissue and lead to diffusion problems similarly associated with the infusion catheter. In addition, these extravascular methods are very invasive and can not be applied to inaccessible vessels.

In each case, the dilution or "washing-out" of the therapeutic agent is a major disadvantage. This "washing-out" can potentially result in the removal of therapeutic agent from the desired treatment site before an effective amount has been absorbed by the diseased vessel. This not only reduces the effectiveness of the treatment by preventing the therapy from reaching the target site, but it also results in the constant discharge of therapeutic agent into the blood stream where it can potentially cause serious side effects. To offset the dilution, an increased volume or concentration is often used which further intensifies concerns for possible side effects.

Another concern associated with known methods for the local delivery of very potent therapeutic agents, such as paclitaxel, is that too much drug is absorbed into the vessel wall due to a high local concentration or too little drug is absorbed into the vessel wall due to a low local concentration. Many drugs have a narrow concentration window at which the drug is effective. A slightly higher concentration can have toxicity effects and a slightly lower concentration can render the treatment ineffective. In order to provide an efficacious concentration to the treated site, a homogeneous delivery of the drug to the treatment site is desired. Without this homogeneous delivery, the administration of such medication often produces adverse side effects or results in some vessel regions where the disease is not sufficiently treated or prevented.

Thus, a need exists for improved methods for the site-specific delivery of therapeutic agents to the vascular system.

SUMMARY

The present disclosure, in one embodiment, is directed to a catheter for site-specific delivery of a therapeutic agent to a blood vessel of a patient. The catheter of the present disclosure, due to the placement of the lateral apertures, allows for the therapeutic agent to be delivered homogeneously to fill the length of a variable treatment window in the vessel. The catheter is comprised of an elongated shaft having at least one inner shaft, at least one outer shaft, a distal end and a proximal end; proximal and distal vessel-conforming balloons, each of which is separately positionable and inflatable which when inflated substantially restricts blood flow in the vessel and creates a treatment window of a defined but variable length for delivery of the therapeutic agent; at least one marker band adjacent to the proximal balloon and at least one marker band adjacent to the distal balloon; and at least one lateral aperture suitable for delivery of the therapeutic agent positioned in the treatment window so as to provide a homogeneous concentration of the therapeutic agent to the treatment window. The lateral aperture can be located in either the inner shaft or the outer shaft. The presence of the lateral apertures, and more specifically, the position, diameter, number and frequency of the lateral apertures, allows for maximum homogeneity of the distribution of therapeutic agent throughout the treatment window.

Another embodiment of the present disclosure is directed to a method of site-specific delivery of a therapeutic agent to a blood vessel of a patient comprising: a) inserting a catheter into the vessel, wherein said catheter comprises at least one inner shaft, at least one outer shaft; proximal and distal vessel-conforming balloons; and at least one lateral aperture; b) inflating the proximal balloon to substantially restrict blood flow through the vessel; c) delivering the therapeutic agent through the lateral aperture to provide a homogeneous concentration of the therapeutic agent to the vessel; d) inflating the distal balloon to form a treatment window for a time sufficient to provide a therapeutically effective amount of the therapeutic agent to the vessel.

Also included as an embodiment of the present disclosure is an in vitro method for determining homogeneity of drug delivery. The method comprises the steps of a) placing a tubular member comprising a liquid of viscosity similar to the viscosity of blood in the path length of an optical sensor, b)

delivering a dye of known concentration to the tubular member, and c) determining the concentration of dye along a treatment length.

BRIEF DESCRIPTION OF THE DRAWINGS

The accompanying drawings, which are incorporated herein and constitute part of this specification, illustrate exemplary embodiments of the present disclosure, and, together with the general description given above and the detailed description given below, serve to explain the features of the present disclosure.

FIG. 2A and FIG. 2B show the variable length of the treatment window.

FIG. 4A shows the guidewire in place and the distal leak path closed, whereas FIG. 4B shows the guidewire in the distal position and the distal leak path open. The flow of therapeutic agent is depicted as arrows from the lateral apertures.

FIGS. 5A and 5B show a partial cross-sectional view of the double balloon catheter showing the distal leak path with the guidewire in place (FIG. 5A) and with the distal leak path open (FIG. 5B) positioned in a branched vessel. The flow of therapeutic agent is depicted as arrows from the lateral aperture.

FIGS. 6A and 6B, show a partial cross-sectional view of the double balloon catheter in a vessel delivering therapeutic agent. FIG. 6A shows a double balloon catheter without lateral apertures. FIG. 6B shows a double balloon catheter with four lateral apertures helically positioned 90 degrees apart. The flow of therapeutic agent is depicted as arrows from the lateral apertures.

FIGS. 7A and 7B show a plan view of the double balloon catheter showing lateral apertures disposed on the outer shaft.

FIGS. 9A, 9B and 9C, show a plan view of the inner shaft and cross-sectional views of the inner shaft with the distal leak path and distal balloon inflation skive.

DETAILED DESCRIPTION OF EMBODIMENTS

Unless defined otherwise, all technical and scientific terms used herein have the same meanings as commonly understood by one of ordinary skill in the art to which this present disclosure belongs. Although any methods and materials similar or equivalent to those described herein can be used in the practice or testing of the present disclosure, the preferred methods, devices, and materials are now described. All publications and patent applications cited herein are incorporated herein by reference in their entirety. Nothing herein is to be construed as an admission that the present disclosure is not entitled to antedate such disclosure by virtue of prior invention.

It must be noted that as used herein and in the appended claims, the singular forms "a," "an," and "the" include plural references unless the context clearly dictates otherwise.

"All numerical designations", e.g., temperature, time, concentration, and molecular weight, including ranges, are approximations which are varied (+) or (−) by increments of less than 25%, or less than 10%. It is to be understood, although not always explicitly stated that all numerical designations are preceded by the term "about". The term "about" is intended to include values which are varied by (+) or (−) less than 25%, or less than 10%. It also is to be understood, although not always explicitly stated, that the reagents described herein are merely exemplary and that equivalents of such are known in the art.

Device for Site-Specific Delivery of a Therapeutic Agent

Figure 1:
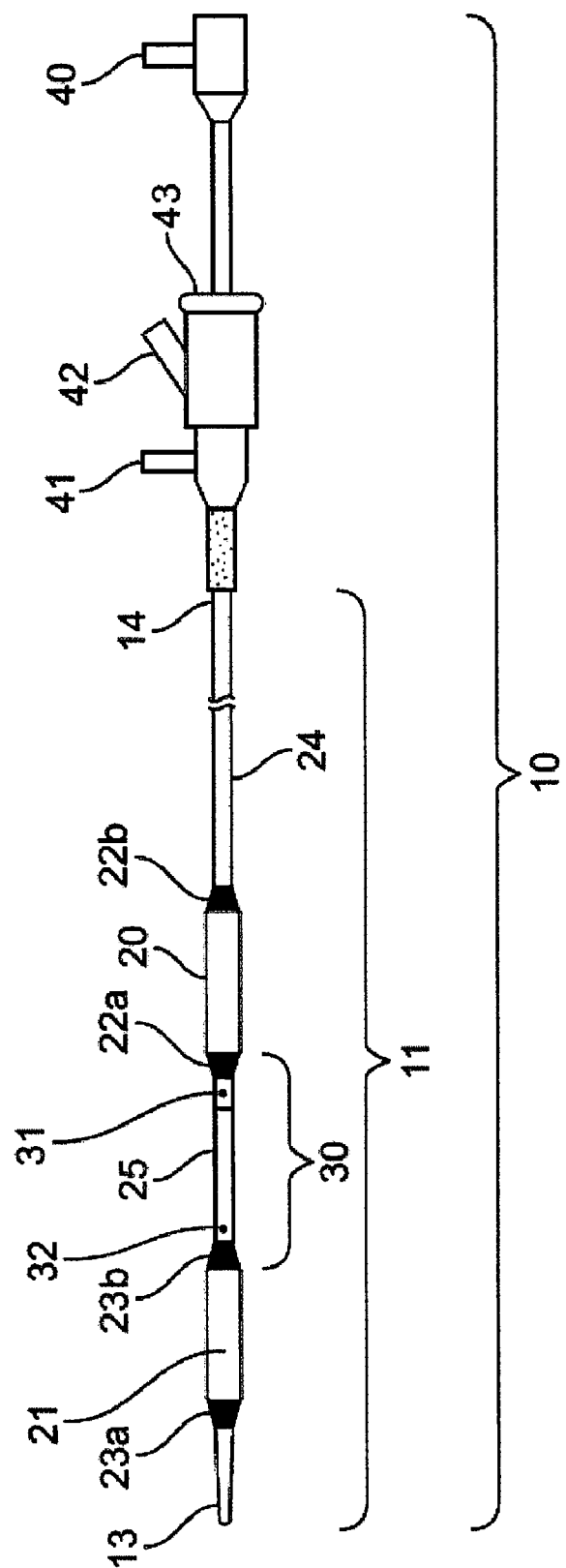
FIG. 1 is a schematic view of the double balloon catheter of the present disclosure.

In one embodiment, as shown schematically in FIG. 1, the present disclosure is directed to a catheter 10 having an elongated shaft 11 with at least one inner lumen, a distal end 13, and a proximal end 14. At the distal end 13 are proximal and distal vessel-conforming balloons, 20 and 21, respectively, that can be inflated in a blood vessel until the balloons conform to an inner surface of the blood vessel to inhibit the flow of blood through the blood vessel and to form a treatment window between the balloons 20 and 21 before delivering a therapeutic agent to the treatment window through an aperture defined in the elongated shaft 11 as described in greater detail below. In any configuration, the tubing of the catheter shaft 11 may be extruded from plastic materials, e.g. thermoplastics, polyimides, polyvinyl chlorides, polyethylenes, polyurethanes, polyesters, polypropylenes, polyurethane urea, polyurethane-silicone block copolymers, fluorinated polyurethane, fluorinated polyurethane urea, or the like. The tubing may consist of several layers of material that may be the same or different. The catheter shaft 11 may be extruded or formed having a variety of lumen cross-sections, including circular or elliptic lumens. Further, as shown in FIGS. 1, 2A, 2B, and 7B, the catheter 10 may be equipped with a distal balloon inflation port 40 for the inflation of the distal balloon 21 and a proximal balloon inflation port 41 for inflation of the proximal balloon 20, rendering the proximal 20 and distal 21 balloons separately inflatable. The "vessel-conforming balloons" are balloons that can be inflated at a pressure less than that to deform the vessel 5 wall. The vessel-conforming balloons may be inflated at a pressure of less than about 15 psi in the vessel.

In one embodiment, the catheter shaft 11 comprises an inner 25 and outer 24 catheter shaft wherein the proximal and distal end of the inner shaft 25 extend beyond the proximal and distal end of the outer shaft 24. The proximal balloon 20 is attached to the distal end of the outer shaft 24. The proximal balloon 20 is in fluid communication with the proximal balloon inflation port 41. The distal balloon 21 is attached to the distal end of the inner shaft 25. The distal balloon 21 is in fluid communication with the distal balloon inflation port 40.

The balloon material is selected to be flexible, such that the balloon, when inflated, is compliant. In one embodiment, the material is of a composition which is based on styrenic olefinic rubber and hydrogenated isoprene, such as that sold under the trade name ChronoPrene™, available from CT Biomaterials, a division of CardioTech International, Inc.

ChronoPrene™ includes the additives polypropylene as a reinforcing agent, and mineral oil as a plasticizer and processing agent. The balloon material, in one embodiment, is sterilizable and biocompatible. The contemplated thickness of the balloon material is in the range of about 0.001 inches to about 0.010 inches ("in"), and is preferably about 0.005 inches. In a preferred embodiment, the inflated balloons substantially conform to the vessel.

The characteristics of the balloon material, including its material, shape, size and the manner in which it is formed and applied relative to either the outer shaft 24 or the inner shaft 25, are selected such that balloon, when inflated, readily takes the path of least resistance within the blood vessel, and minimally impacts the shape and integrity of the vessel and causes little or no barotrauma. This reduces the threat of acute vessel rupture, and/or of subsequent restenosis. At the same time, the functionality of the balloon is unhindered and serves to effectively occlude or impede blood flow. The diameter of the balloons can range from about 3 millimeters to about 30 millimeters as dependent on the diameter of the treatment site. In one embodiment, the diameter of each balloon is about 3 millimeters ("mm"). Alternatively, the diameter of each balloon is about 4 millimeters, or alternatively about 5 millimeters, or alternatively about 6 millimeters, or alternatively about 7 millimeters, or alternatively about 8 millimeters, or alternatively about 9 millimeters, or alternatively about 10 millimeters, or alternatively about 12 millimeters, or alternatively about 15 millimeters, or alternatively about 20 millimeters, or alternatively about 25 millimeters, or alternatively about 30 millimeters. The balloon, or at least a portion thereof, will thus be more deformable than the vascular wall, even when that vascular wall is diseased and is of compromised strength and stiffness.

Factors to consider in providing the necessary balloon performance are elongation and tensile strength of balloon material. ChronoPrene™ 15A can be used, which has a Hardness-Shore A ASTM D2240 (3 sec.) rating of about 15, a specific gravity of about 0.89, tensile strength of about 600 psi, and elongation of greater than about 1,000%. Alternatively, ChronoPrene™ 40A can be used, which has a Hardness-Shore A ASTM D2240 (3 sec.) rating of about 40, a specific gravity of about 0.90, tensile strength of about 700 psi, and elongation of about 500%. The balloon material may be pre-stretched or otherwise mechanically and/or thermally manipulated to improve performance. In one embodiment, the balloon material may include a blend of silicone and polyurethane, such as the blend commercially available under the name of Polyblend®.

As depicted in FIGS. 2A and 2B, the inner shaft 25 moves slideably within outer shaft 24, thus adjusting the space between distal balloon 21 and proximal balloon 20. The term "treatment window" is intended to refer to the region between the distal end of the proximal balloon 20 and the proximal end of the distal balloon 21. The length of the treatment window 30 is intended to be adjustable such that it allows for treatment of a sufficient length of the diseased vessel, with the ability to avoid exposing normal vessel to the therapeutic agent. As illustrated in FIGS. 2A and 2B, the length of the treatment window 30 may be varied by sliding the inner shaft 25 into the outer shaft 24. The length of the treatment window 30 can range from about 2 centimeters to about 25 centimeters. The treatment window 30 is secured by locking adapter 43.

In one embodiment, at least one marker band 22b is located proximally to the proximal balloon 20 and at least one marker band 23a is located distally to the distal balloon 21. In one embodiment, at least one marker band is positioned immediately adjacent to at least one of the proximal and distal balloons 20, 21. It may, in some cases, be desirable to have additional marker bands present on the catheter shaft 11 to aid visualization. Additional marker bands 22a and 23b can be placed adjacent to ends of the proximal and distal balloons 20, 21 to provide the operator a complete view of the treatment window 30. Referring to FIGS. 1, 2A and 2B, in one embodiment, radiopaque marker bands 22a, 22b, 23a and 23b are disposed adjacent to both the proximal and distal ends of the vessel-conforming balloons 20 and 21. Marker bands 22a, 22b, 23a and 23b may be of metallic or polymeric material and are typically a metal alloy ring such as platinum, nitinol, and/or gold rings which can be visualized via fluoroscopy. As depicted in FIG. 7A, marker band 22a is inside the balloon and proximal to the point of balloon adhesion 35 (shown as a wrapping).

Figure 11:
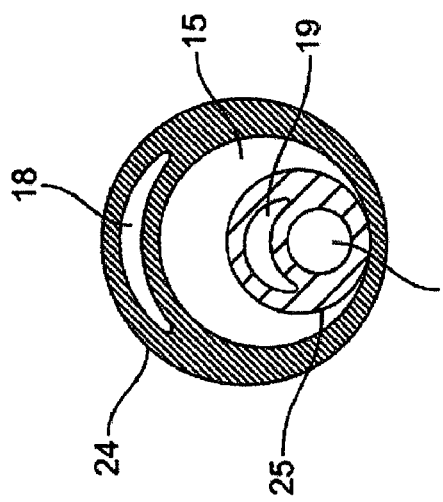
FIGS. 10, 11 and 12 show cross-sectional views of various embodiments of the catheter lumen structure.
Figure 12:
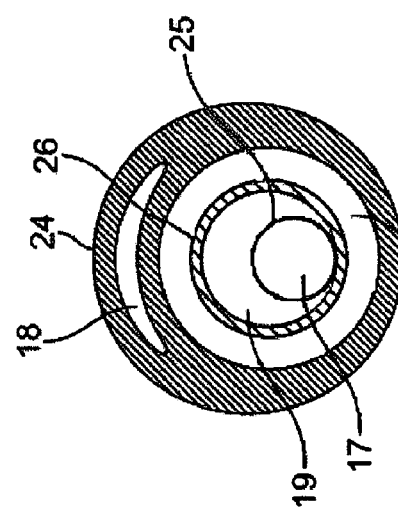
Figure 10:
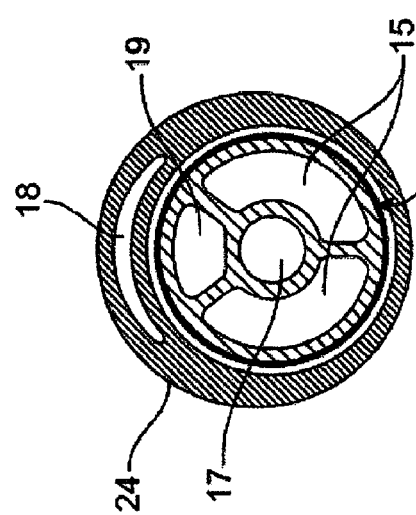

The inner shaft 25 and outer shaft 24 of catheter 10 preferably comprise one or more axially extending co-linear lumens as depicted in cross-sectional views shown in FIGS. 10, 11 and 12. A drug delivery conduit and/or lumen 15 may be located coaxially with the inner shaft 25. Various lumens may be present to function as balloon inflation/deflation lumen (18 and 19), guidewire lumen 17, and/or drug delivery conduit 15. The lumen may be oriented together in a variety of configurations. The multiple lumen can be in concentric and non-concentric arrangements and can extend along different portions of the catheter 10.

Figure 3:
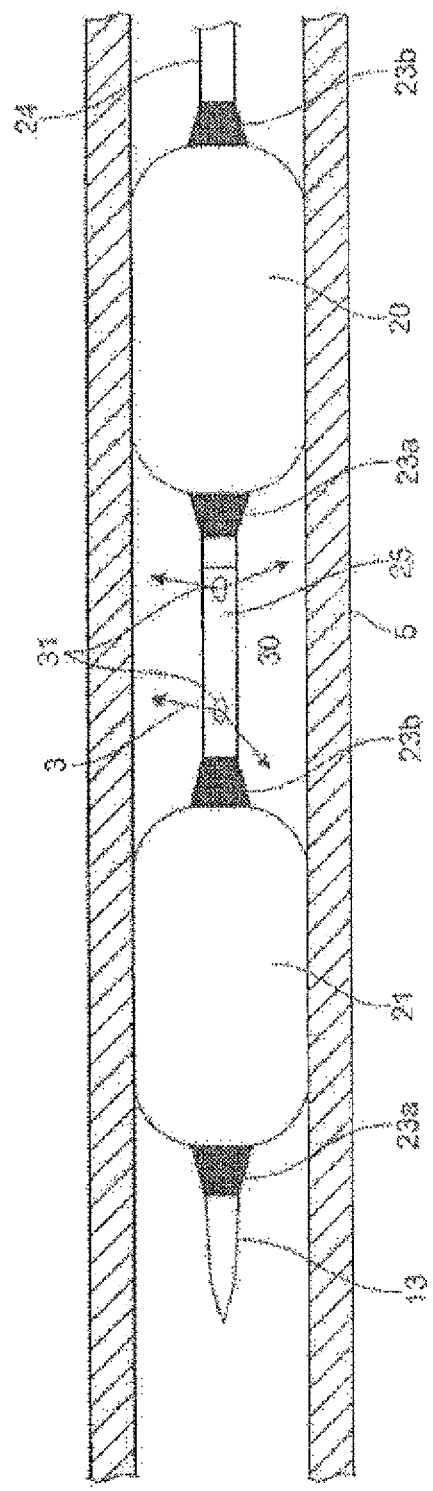
FIG. 3 shows a partial cross-sectional view of the double balloon catheter of the present disclosure in a vessel. The flow of therapeutic agent is depicted as arrows from the lateral aperture.

The catheter 10 disclosed herein allows for the therapeutic agent to be substantially homogeneous throughout the treatment window 30. The position, diameter, number and frequency of lateral or delivery apertures 31 results in the substantially homogeneous filling of the treatment window 30. FIG. 3 depicts a catheter positioned in a vessel 5 having two lateral apertures 31 located within the treatment window 30 for the delivery of the therapeutic agent 3. The lateral apertures 31 as shown in FIG. 3, are in fluid communication with the lumen of the inner shaft 25. Lateral apertures 31 located within the treatment window 30 can be defined within either the outer 24 or inner 25 shaft such that the therapeutic agent is delivered homogeneously to the treatment window 30.

The terms "homogeneous" and "substantially homogeneous" is intended to refer to the therapeutic agent having less than about 10% concentration variability from the mean concentration over the length of the treatment window 30 so that the vessel is substantially uniformly exposed to the agent. In one embodiment, the therapeutic agent has a less than about 10% concentration variability from the mean concentration over the length of the treatment window 30. Alternatively, the therapeutic agent has a less than about 9% concentration variability from the mean concentration over the length of the treatment window 30, or alternatively, less than about 8%, or alternatively, less than about 7%, or alternatively, less than about 6%, or alternatively, less than about 5%, or alternatively, less than about 4%, or alternatively, less than about 3%, or alternatively, less than about 2%.

Figure 4A:
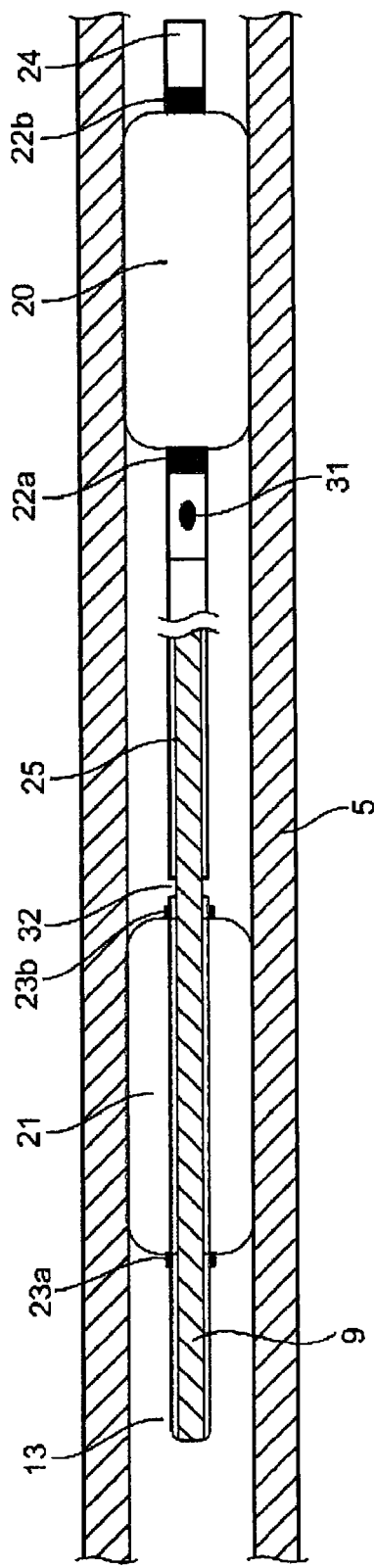
FIGS. 4A and 4B show a partial cross-sectional view of the double balloon catheter showing the distal leak path positioned in a vessel.
Figure 4B:
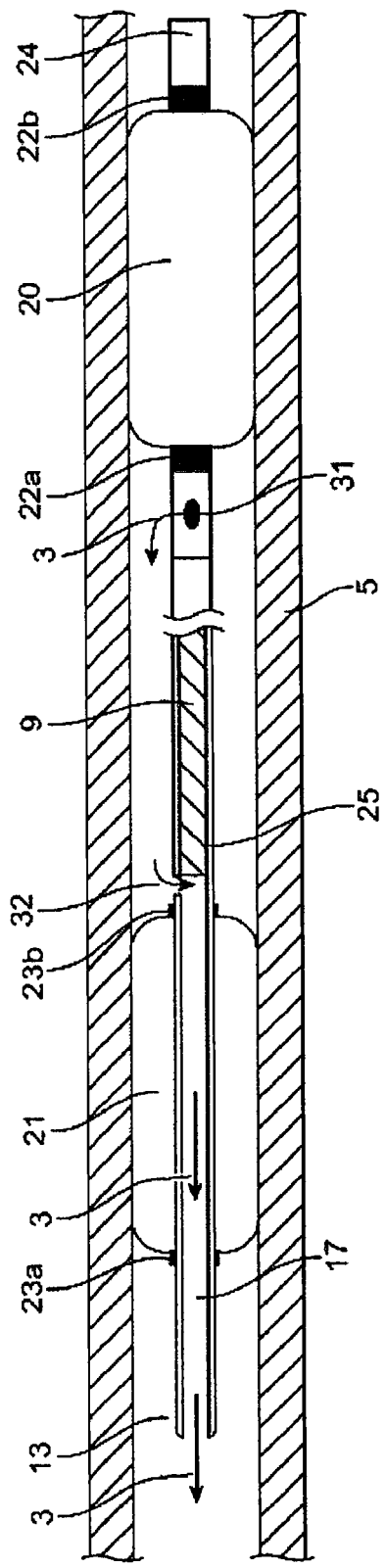

FIGS. 4A, 4B, 5A, and 5B depict catheters positioned in a vessel 5 having one lateral aperture 31 in fluid communication with the outer shaft 24 for the delivery of the therapeutic agent 3 to the treatment window 30. The homogeneous delivery of therapeutic agent 3 to the treatment window 30 is facilitated by a distal leak path or a drain passage 32 which is in fluid communication with the inner shaft 25. In particular, the inner shaft 25 defines a distal opening, a drug passing lumen, and one or more distal leak apertures that are in fluid communication to form the distal leak path 32, illustrated, for example, with the distal progression of arrows through the inner shaft 25 seen in FIGS. 4B and 5B. The treatment window 30 is isolated upon inflation of the proximal balloon 20 and distal balloon 21. When the guidewire 9 is in place, the distal leak path 32 is closed (FIGS. 4A and 5A). Retraction of the guidewire exposes the distal leak path 32. As shown in FIG. 4B, perfusion of the therapeutic agent 3 would displace the fluid present in the isolated treatment window 30 of the vessel 5, allowing for the homogeneous delivery of therapeutic agent 3 to the treatment window 30. Upon delivery of therapeutic agent 3, the guidewire 9 can be repositioned such that the distal leak path 32 is closed and the treatment window 30 is isolated for the duration of the treatment.

The distal leak path 32 also allows for a homogeneous delivery of therapeutic agent 3 to the treatment window 30 of a branched vessel 6 (FIG. 5B). In this case, a constant flow of therapeutic agent 3 from the lateral aperture 31 to the treatment window 30 and out the distal leak path 32 would substantially limit the exposure of the branched vessel 6 to the therapeutic agent 3.

FIG. 6A depicts a catheter wherein the therapeutic agent is delivered to the treatment window 30 via an annulus between the outer shaft 24 and inner shaft 25 (i.e. without lateral apertures). This configuration results in a laminar flow of the therapeutic agent along the path of the catheter. This delivery does not provide a homogeneous concentration of therapeutic agent to the treatment window 30. The laminar flow of therapeutic agent results in a radial concentration gradient of therapeutic agent where the most concentrated solution is at a radius close to the inner shaft 25, and a lower concentration solution is out at the inner wall of the vessel 5. In addition, the laminar flow of therapeutic agent does not displace the blood present in the treatment window 30. Specifically, the laminar flow does not displace the blood adjacent to the distal end of the proximal balloon 20 by therapeutic agent. This configuration results in both dilution and non-homogeneous delivery of therapeutic agent.

As stated above, the lateral apertures 31 located within the treatment window 30 provide a substantially homogeneous filling of the treatment window 30. Specifically, the position, frequency, number and diameter of the lateral apertures 31 can be tailored to homogeneously deliver the therapeutic agent to the treatment window 30 by displacing the volume of blood in the vessel 5 while avoiding mixing the therapeutic agent with the blood. This allows for the concentration of therapeutic agent in the vessel 5 to remain at substantially the same concentration as was delivered through the drug delivery conduit 15.

FIG. 6B depicts one embodiment of a catheter as disclosed herein having lateral apertures 31 disposed between the proximal 20 and distal 21 balloons on the inner shaft 25. FIGS. 7A, 7B, 8A and 8B depict another embodiment having lateral apertures 31 disposed between the proximal 20 and distal 21 balloons on the inner shaft 25. The lateral apertures can be located in the outer 24 or inner 25 shaft depending on which is in fluid communication with the drug delivery conduit 15. The lateral apertures 31 allow the drug infusion to flow radially as it passes the proximal balloon 20 (in a path orthogonal to the stream of flow within the catheter 10). The lateral apertures 31 are designed such that laminar flow is preserved, and blood is gently displaced without mixing of therapeutic agent and blood. This allows the therapeutic agent concentration within the entire treatment window 30 to be very close to the original concentration of the infusate.

Figure 8C:
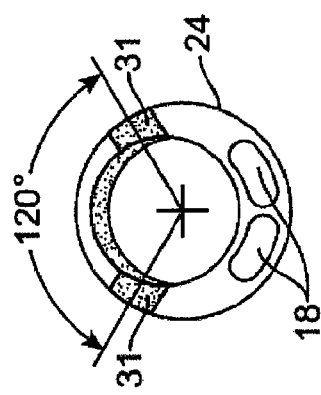
FIGS. 8A, 8B and 8C show a plan view of the outer shaft with lateral apertures positioned in a plane 120 degrees apart.
Figure 8A:
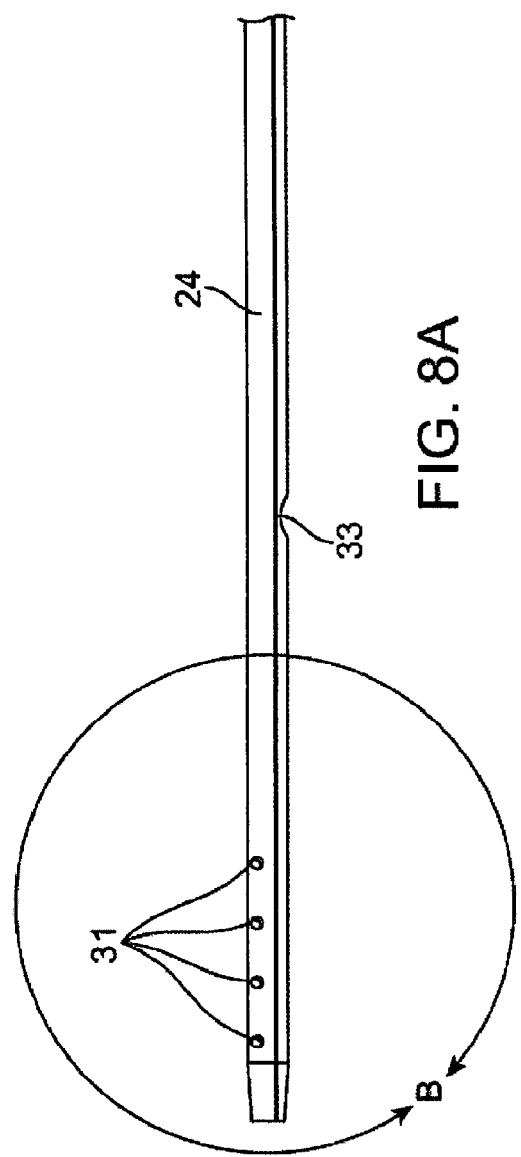
Figure 8B:
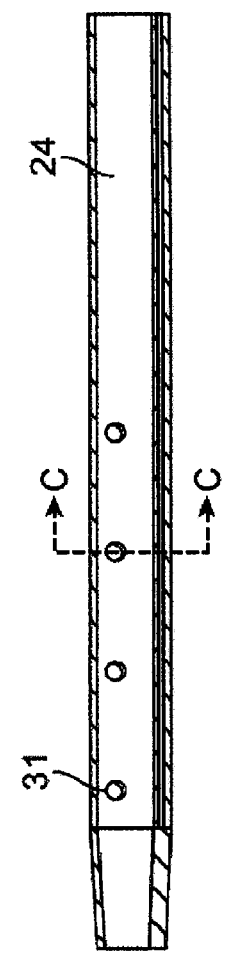

The position of the lateral apertures 31 can be at any location within the treatment window 30 depending on the configuration of the lumen within the outer 24 and inner 25 shaft. In some embodiments, the lateral apertures 31 are positioned linearly along the length if the axis of the catheter shaft (FIGS. 7A and 7B). In some embodiments, the lateral apertures are in a plane and placed at an angle of about 90 to about 180 degrees apart. This embodiment is exemplified in FIGS. 8A, 8B and 8C for example, wherein eight lateral apertures are shown on the outer shaft and are positioned 120 degrees apart. The proximal balloon inflation skive 33 is positioned opposite the lateral apertures (FIG. 8A, balloon and marker bands not shown). In some embodiments, the lateral apertures 31 are positioned helically along the axis of the catheter (FIG. 6B). In one embodiment, the lateral apertures 31 are helically positioned at an angle of about 90 to about 180 degrees apart from one another. In one embodiment, the distance between the lateral apertures 31 is about 1 to about 5 mm. In some embodiments, the distance between the lateral apertures 31 is about 1 mm, or alternatively, about 2 mm, or alternatively, about 3 mm, or alternatively, about 4 mm, or alternatively, about 5 mm. In one embodiment, the distance between the lateral apertures 31 is about 2.8 mm.

The number of lateral apertures 31 may be adjusted in order to increase the homogeneity and/or decrease the delivery time of the therapeutic agent. In certain embodiments, the number of lateral apertures 31 is between 1 and about 20. In some embodiments, the number of lateral apertures 31 is about 4, or alternatively, about 6, or alternatively, about 8, or alternatively, about 10, or alternatively, about 12, or alternatively, about 14, or alternatively, about 16, or alternatively, about 18, or alternatively, about 20.

The diameter of the lateral apertures 31 may also be adjusted to increase the homogeneity and/or decrease the delivery time of the therapeutic agent. In one embodiment the diameter of the lateral apertures 31 is about 0.001 inches to about 0.050 inches. Alternatively, the diameter of the lateral apertures 31 is about 0.005 inches to about 0.040 inches, or alternatively, about 0.005 inches to about 0.030 inches, or alternatively, about 0.010 inches to about 0.025 inches, or alternatively, about 0.015 inches to about 0.020 inches, or alternatively, about 0.018 inches. In one embodiment, the diameter of the distal lateral apertures is greater than the diameter of the proximal lateral apertures so as to balance the flow rates through the apertures as the pressure in drug delivery conduit 15 decreases distally. The diameter of the lateral apertures 31 may be balanced with the number of lateral apertures 31 in order to avoid a high velocity of therapeutic agent delivery being delivered to the treatment window 30 which could result in dilution of the therapeutic agent and blood remaining in the treatment window 30.

Referring to FIGS. 4A and 4B, in one embodiment, the catheter contains a distal leak path 32. In certain embodiments, the distal leak path 32 may comprise a skive or hole which permits the treatment window 30 to be in fluid communication with the central or guidewire lumen 17 at the very distal tip 13. A "skive" can include a channel or a scalloped or gouged opening in the wall of a shaft. This skive provides a low resistance path for the therapeutic agent out of the treatment window 30 through the distal tip 13. With the guidewire 9 in place, the distal leak path 32 remains closed and provides a fluid tight seal as shown in FIG. 4A. The distal leak path 32 can be opened by pulling the guidewire 9 proximally. FIG. 4B shows the distal leak path in the open position.

In some embodiments, the distal tip 13 is constructed from the inner shaft 25 by smoothing the radius and closing the inflation lumen 19. Therefore, the distal tip 13 may have a diameter slightly less than the diameter of the inner shaft 25. In a preferred embodiment, the catheter tip 13 is a blunt, tapered, smooth, atraumatic, and free of jagged edges to prevent tissue damage during advancement of the catheter. As shown in FIG. 4A, with the guidewire 9 in place, the distal leak path 32 remains closed and provides a fluid tight seal, thus isolating the treatment window. When the guidewire 9 is pulled proximally (FIG. 4B) the treatment window 30 is in fluid communication with the vessel 5 lumen. If there is a continual flow of therapeutic agent 3 into the treatment window 30, the therapeutic agent may be released through the distal leak path 32 (FIGS. 4A, 4B, 5A and 5B). The distal leak path 32 is of sufficiently small diameter as not to disrupt the attenuation of blood flow. As shown in FIG. 9A, in some embodiments, the distal leak path 32 is placed about 2 to 5 mm from the proximal end of the distal balloon 21 on the inner shaft 25. Alternatively, in some embodiments, the distal leak path 32 is placed about 2 mm from the proximal end of the distal balloon 21 on the inner shaft 25, or alternatively, about 3 mm, or alternatively, about 4 mm, or alternatively about 5 mm. In one embodiment, the distal leak path 32 is placed about 4 mm from the proximal end of the distal balloon 21 on the inner shaft 25. FIGS. 9B and 9C (cross-sections "B" and "C" in 9A) show the distal balloon inflation skive 34 in fluid communication with the distal balloon inflation lumen 19 and the distal leak path 32 in fluid communication with the guidewire lumen 17.

In some cases, the diseased vessel in need of treatment may have branched vessels 6 or side vessels. In such cases, in order to avoid the delivery of the therapeutic agent to undesired locations, it may be necessary to use distal leak path 32. FIG. 5A depicts the delivery of a therapeutic agent (arrows) to a treatment window 30 with a branched vessel 6 without the use of a distal leak path 32. As shown, the therapeutic agent would likely flow into the undesired branch vessel 6 and both lessen the effectiveness of the therapeutic treatment on the main vessel 5 (distal to the branch vessel 6) and expose potentially healthy branch vessel to therapeutic agent. FIG. 5B shows the distal leak path 32 in the open position (i.e., with the guidewire 9 in the proximal position exposing the treatment window 30 to the guidewire lumen 17). The distal leak path 32 provides a low resistance path for the therapeutic agent out of the treatment window 30 through the distal tip 13, such that the agent preferentially flows to the distal balloon 21 (filling the full treatment window 30) rather than flowing through the branched vessel 6. The distal leak path 32 can be opened by pulling the guidewire 9 proximally. If there is continual flow into the treatment window 30, the therapeutic agent is released through the distal leak path and does not substantially infuse into undesired branch vessels. With the guidewire 9 in place, the distal leak path 32 remains closed and provides a fluid tight seal. As shown in FIG. 9A, in some embodiments, the distal leak path 32 is placed about 2 to 5 millimeters ("mm") from the proximal end of the distal balloon 21 on the inner shaft 25. Alternatively, in some embodiments, the distal leak path 32 is placed about 2 mm from the proximal end of the distal balloon 21 on the inner shaft 25, or alternatively, about 3 mm, or alternatively, about 4 mm, or alternatively about 5 mm. In one embodiment, the distal leak path 32 is placed about 4 mm from the proximal end of the distal balloon 21 on the inner shaft 25.

FIGS. 9B and 9C show cross sectional views of the inner shaft 25 with the distal balloon inflation skive 34 (FIG. 9B) and the distal leak path 32 (FIG. 9C). Further exemplary embodiments are disclosed below. FIGS. 10, 11 and 12 show various cross-sectional views of multiple lumens 15, 17, 18 and 19 in accordance with the present disclosure.

In one embodiment as shown in FIG. 10, more than one drug delivery conduit 15 is located coaxially within inner shaft 25 along with the distal balloon inflation lumen 19 and central or guidewire lumen 17. The outer shaft 24 houses the proximal balloon inflation lumen 18 as well as inner shaft 25. The drug delivery conduit 15 is in fluid communication with both the drug delivery port 42 and at least one lateral aperture 31 (shown in FIG. 1) positioned proximally to the distal balloon 21. With the drug delivery conduit in the inner shaft 25 as shown in FIG. 10, lateral apertures can be created along the full length of the inner shaft 25 up to the distal balloon 21. The total cross sectional area for drug infusion in this design is about 0.0005 to about 0.0030 in$^2$. In one embodiment, the total cross sectional area for drug infusion in this design is about 0.00110 in$^2$.

In another embodiment, as shown in FIG. 11, the outer shaft 24 houses proximal balloon inflation lumen 18. Concentrically within the outer shaft 24 is the drug delivery conduit 15, which contains the inner shaft 25 concentrically within. The inner shaft 25 houses the distal balloon inflation lumen 19 and central or guidewire lumen 17. In this configuration, lateral apertures 31 can be positioned distal to the proximal balloon 20 to allow for homogeneous delivery. In this embodiment, the distal leak path can be placed in the inner shaft 25 to maintain segment filling after occlusion, even in the presence of low-resistance side branches within the treatment window 30. The use of the annulus between the inner and outer shaft for drug delivery in this embodiment gives the total cross sectional area for drug infusion as about 0.0005 to about 0.0030 in$^2$. In one embodiment, the total cross sectional area for drug infusion in this design is about 0.00133 in$^2$.

In yet another embodiment, as shown in FIG. 12 the outer shaft 24 houses proximal balloon inflation lumen 18. Within the outer shaft 24 are the middle shaft 26 and the inner shaft 25. In some embodiments, the inner shaft 25 is affixed to the middle shaft 26 for the majority of the length of the catheter. It is contemplated that the inner shaft 25 can be affixed to the middle shaft 26 at the proximal and/or distal ends. It is further contemplated that the inner shaft can be affixed to the middle shaft 26 with either the ends of the inner and middle shaft flush, or with the distal tip of the inner shaft 25 extended beyond the distal end of the middle shaft 26. The drug delivery conduit 15 is the annulus between the outer shaft 24 and the middle shaft 26. The distal balloon inflation lumen is the annulus between the inner shaft 25 and the middle shaft 26. The inner shaft 25 houses the central or guidewire lumen 17. In this configuration, the inner and middle shafts can be extruded as simple cylinders, and use of the annuli between the three concentric shafts maximizes cross sectional area for distal balloon inflation and drug infusion. The total cross sectional area for drug infusion in this design is about 0.0005 to about 0.0030 in$^2$. In one embodiment, the total cross sectional area available for drug infusion in this configuration is about 0.00120 in$^2$.

In one embodiment, the drug infusion rate for the catheters 10 disclosed herein is from about 0.50 milliliters per second ("ml/s") to about 2.0 ml/s at a pressure of about 40 psi, from about 0.35 ml/s to about 1.4 ml/s at a pressure of about 30 psi and from about 0.20 ml/s to about 1.0 ml/s at a pressure of about 20 psi. Drug infusion rates may vary depending on the path of the catheter. A catheter 10 within a vessel 5 having one or more bends, may display a lower drug infusion rate than the same catheter 10 in a straight vessel 5. The drug infusion rate may also vary based on factors such as the configuration of the catheter lumen, the viscosity of the therapeutic agent, and the number and diameter of the lateral apertures 31. The viscosity of the therapeutic agent will vary depending on the physical properties, concentration, solvent used, etc. Determining the viscosity of the therapeutic agent is within the skill of one in the art. The catheter configurations shown in FIGS. 10, 11 and 12 provide drug infusion rates of about 0.60 ml/s, about 1.80 ml/s, and about 1.60 ml/s, respectively, at a pressure of about 40 psi, about 0.45 ml/s, about 1.350 ml/s, and about 1.25 ml/s, respectively, at a pressure of about 30 psi, and about 0.30 ml/s, about 0.90 ml/s, and about 0.80 ml/s, respectively, at a pressure of about 20 psi. In one embodiment, the drug infusion rate for the catheter is about 1.0 ml/s at a pressure of up to 40 psi. However, drug infusion rates of from about 0.10 ml/s to about 5.0 ml/s are contemplated.

Method for the Site-Specific Delivery of a Therapeutic Agent

The catheter 10 of the present disclosure may be used for the site specific delivery of a therapeutic agent 3 to a blood vessel 5 of a patient. Now referring to FIG. 1, a clinician inserts the elongated shaft 11 of catheter 10 into the patient's vessel 5 through an access point, such as the femoral artery, until the desired treatment site in the vessel 5 is reached. The proximal balloon 20 is positioned proximal to the desired treatment site and the distal balloon 21 is positioned distal to the treatment site to create the treatment window 30. This is done by axially moving the distal inflation port 40 relative to the proximal inflation port 41 and thus adjusting insertion of inner shaft 25 into outer shaft 24.

The placement of the proximal 20 and distal 21 balloons to form the treatment window 30 is facilitated by visualization of the radiopaque marker bands 22a, 22b, 23a and 23b located adjacent to the balloons 20 and 21. Optionally, additional marker bands may be fastened onto the catheter shaft 11 for added visualization. The length of the treatment window 30 can be adjusted by the clinician so the treatment area is between the proximal balloon 20 and distal balloon 21 and treats a sufficient amount of the diseased vessel with the ability to avoid treating non-diseased vessel. The length of the treatment window 30 can range from about 2 centimeters to about 25 centimeters. In an alternative embodiment, the treatment window 30 can range from about 2 centimeters to about 20 centimeters, or alternatively from about 2 centimeters to about 15 centimeters, or alternatively from about 2 centimeters to about 10 centimeters, or alternatively from about 2 centimeters to about 5 centimeters. Once adjusted to the desired length, the treatment window 30 is secured by locking adapter 43.

The proximal balloon 20 is first inflated by the operator injecting a fluid into the proximal inflation port 41. It may be advantageous to visualize inflation of the balloon 20 by utilizing an inflation fluid containing a contrast agent. The vessel 5 is sealed and thus isolated from the flow of blood from a proximal location once the proximal balloon 20 is inflated to contact the vessel 5 and at an inflation pressure greater than blood pressure. The fluid may be saline and/or a contrast agent injected by syringe or other inflation device (not shown). Therefore, the proximal balloon 20 substantially restricts the blood flow through the vessel 5. Although it is preferred that the vessel 5 be isolated from the flow of blood from a proximal location, it is to be understood that in some cases it may be desirable to maintain the flow of blood in a substantially attenuated manner. In one embodiment, the proximal balloon 20 is inflated at a pressure low enough so as not to compress against the blood vessel 5, cause barotrauma, or less than that to deform the vessel. In some cases, the proximal balloon 20 is inflated to a pressure of less than about 15 psi in the vessel 5. In a preferred embodiment, the proximal balloon 20 is inflated in less than about 6 seconds. In an alternative embodiment, the proximal balloon 20 is inflated in less than about 8 seconds, or alternatively, about less than 10 seconds.

After inflation of the proximal balloon 20 and sealing of the vessel 5 as described above, the therapeutic agent is delivered to the diseased vessel 5. This is depicted schematically in FIGS. 3, 6A and 6B. The therapeutic agent is injected via syringe (not shown) into the drug injection port 42 which is in fluid communication with the drug delivery conduit 15 and one or more lateral apertures 31. It is preferred that the amount of therapeutic agent delivered is sufficient to substantially and homogeneously fill the treatment window 30. In one embodiment, the treatment window 30 has a concentration of therapeutic agent which is a substantially homogeneous. In one embodiment, the therapeutic agent has a less than about ±10% concentration variability from the mean concentration over the length of the treatment window. Alternatively, the therapeutic agent has a less than about ±9% concentration variability from the mean concentration over the length of the treatment window 30, or alternatively, less than about ±8%, or alternatively, less than about ±7%, or alternatively, less than about ±6%, or alternatively, less than about ±5%, or alternatively, less than about ±4%, or alternatively, less than about ±3%, or alternatively, less than about ±2%. The therapeutic agent may optionally contain a contrast agent mixed in for visualization.

Various therapeutic agents can be with the methods disclosed herein such as antineoplastics, antiplatelets, anticoagulants, antifibrins, antithrombins, antimitotics, anti-proliferatives, anti-inflammatories, antibiotics, limus drugs and antioxidant substances, for example. In one embodiment, the therapeutic agent is delivered at a rate of greater than about 1.0 milliliter/second. Alternatively, the therapeutic agent is delivered at a rate of greater than about 0.8 milliliters/second, or alternatively, greater than about 0.6 milliliters/second or alternatively, greater than about 0.4 milliliters/second or alternatively, greater than about 0.2 milliliters/second.

Examples of antineoplastics include actinomycin D (ActD), paclitaxel, docetaxel and second or third generation taxanes or derivatives and analogs thereof. Examples of antiplatelets, anticoagulants, antifibrins, and antithrombins include, but are not limited to, sodium heparin, low molecular weight heparin, hirudin, argatroban, forskolin, vapiprost, prostacyclin and prostacyclin analogs, dextran, D-phe-pro-arg-chloromethylketone (synthetic antithrombin), dipyridamole, glycoprotein IIb/IIIa platelet membrane receptor antagonist, recombinant hirudin, thrombin inhibitor (available from Biogen located in Cambridge, Mass.), 7E-3B®. (an antiplatelet drug from Centocor located in Malvern, Pa.); tissue plasminogen activator, lanoteplase, reteplase, staphylokinase, streptokinase (SK), tenecteplase and urokinase. Examples of antimitotic agents include methotrexate, azathioprine, vincristine, vinblastine, fluorouracil, adriamycin, and mutamycin, epothilones, and second or third generation taxanes. Examples of cytostatic or antiproliferative agents include angiopeptin (a somatostatin analog from Ibsen located in the United Kingdom), angiotensin converting enzyme inhibitors such as CAPTOPRIL® (available from Squibb located in New York, N.Y.), CILAZAPRIL® (available from Hoffman-LaRoche located in Basel, Switzerland), or LISINOPRIL® (available from Merck located in Whitehouse Station, N.J.). Examples of limus drugs include biolimus, sirolimus, everolimus, tacrolimus, and zotarolimus. Other therapeutic drugs or agents which may be appropriate include calcium channel blockers (such as nifedipine), colchicine, fibroblast growth factor (FGF) antagonists, fish oil (omega 3-fatty acid), histamine antagonists, LOVASTATIN® (an inhibitor of HMG-CoA reductase, a cholesterol lowering drug from Merck), methotrexate, monoclonal antibodies (such as those targeting platelet-derived growth factor (PDGF) receptors), nitroprusside, phosphodiesterase inhibitors, prostaglandin inhibitors including prostaglandin E synthase and prostaglandin E-1 (PGE-1) inhibitors (GlaxoSmithKline, United Kingdom), seramin (a PDGF antagonist), serotonin blockers, steroids, thioprotease inhibitors, triazolopyrimidine (a PDGF antagonist), nitric oxide, alpha-interferon, genetically engineered endothelial cells, dexamethasone, RNAi (RNA interference) molecules and gene vectors.

Preferred therapeutic agents to be used are antiproliferative agents, anti-inflammatory agents, antiplatelet agents, paclitaxel, docetaxel, second or third generation taxanes, limus drugs, sodium heparin, low molecular weight heparin, tissue plasminogen activator, epothilones, monoclonal antibodies (such as those targeting platelet-derived growth factor (PDGF) receptors), RNAi (RNA interference) molecules and gene vectors.

The preceding therapeutic agents are provided by way of example and are not meant to be limiting, as other therapeutic drugs may be developed which are equally applicable for use with the present disclosure. The treatment of diseases using the above therapeutic agents is known in the art. The calculation of dosages, dosage rates and appropriate duration of treatment are previously known in the art.

Once the therapeutic agent has filled the treatment window 30, the distal balloon 21 is inflated by the operator injecting a fluid into the distal inflation port 40. In a preferred embodiment, the distal balloon 21 is inflated in less than about 6 seconds. In an alternative embodiment, the distal balloon 21 is inflated in less than about 8 seconds, or alternatively, less than about 10 seconds. FIG. 3 shows a schematic of the catheter 10 with the proximal balloon 20 and distal balloon 21 inflated within the vessel 5.

The proximal balloon 20 and distal balloon 21 remain inflated for a time sufficient to provide a therapeutically effective amount of the therapeutic agent to the vessel 5. In one embodiment, the therapeutic agent is dispersed or diffused homogeneously throughout the treatment window 30. The treatment time will vary depending on the dosage required by the patent and the concentration of therapeutic agent delivered to the vessel 5. In some embodiments, the treatment time is from about 1 minute to about 60 minutes. In certain embodiments, the treatment time is less than about 60 minutes. In other embodiments, the treatment time is less than about 50 minutes, or alternatively, less than about 40 minutes, or alternatively, less than about 30 minutes, or alternatively, less than about 20 minutes, or alternatively, less than about 10 minutes, or alternatively, less than about 5 minutes, or alternatively, less than about one minute.

Once the desired treatment time has expired, the distal balloon 21 and proximal balloon 20 are deflated. In a preferred embodiment, both balloons are deflated in less than about 8 seconds. Alternatively, the proximal balloon 20 and distal balloon 21 are deflated in less than about 20 seconds, or alternatively, in less than about 15 seconds, or alternatively, in less than about 6 seconds, or alternatively, in less than about 4 seconds. In some cases, depending on the path of the catheter lumen, the proximal balloon 20 and distal balloon 21 are deflated in less than about 60 seconds. The therapeutic agent is washed from the treatment site 30 upon deflation of the proximal balloon 20 and distal balloon 21 as blood flow is restored. Alternatively, the therapeutic agent is aspirated from the treatment window 30. This can be accomplished using suction. Suction can be applied to the drug infusion port 42 prior to the deflation of the proximal balloon 20. The aspiration of the therapeutic agent from the treatment window 30 may be facilitated by the partial deflation of the distal balloon 21.

After treatment is complete, the catheter 10 can optionally be repositioned for subsequent treatment or removed from the patient if the procedure is finished.

The present disclosure is further understood by reference to the following examples, which are intended to be purely exemplary of the present disclosure. The present disclosure is not limited in scope by the exemplified embodiments, which are intended as illustrations of single aspects of the present disclosure only. Any methods that are functionally equivalent are within the scope of the present disclosure. Various modifications of the present disclosure in addition to those described herein will become apparent to those skilled in the art from the foregoing description. Such modifications fall within the scope of the appended claims.

EXAMPLES

Example 1

Vascular Absorption of Paclitaxel

Figure 13:
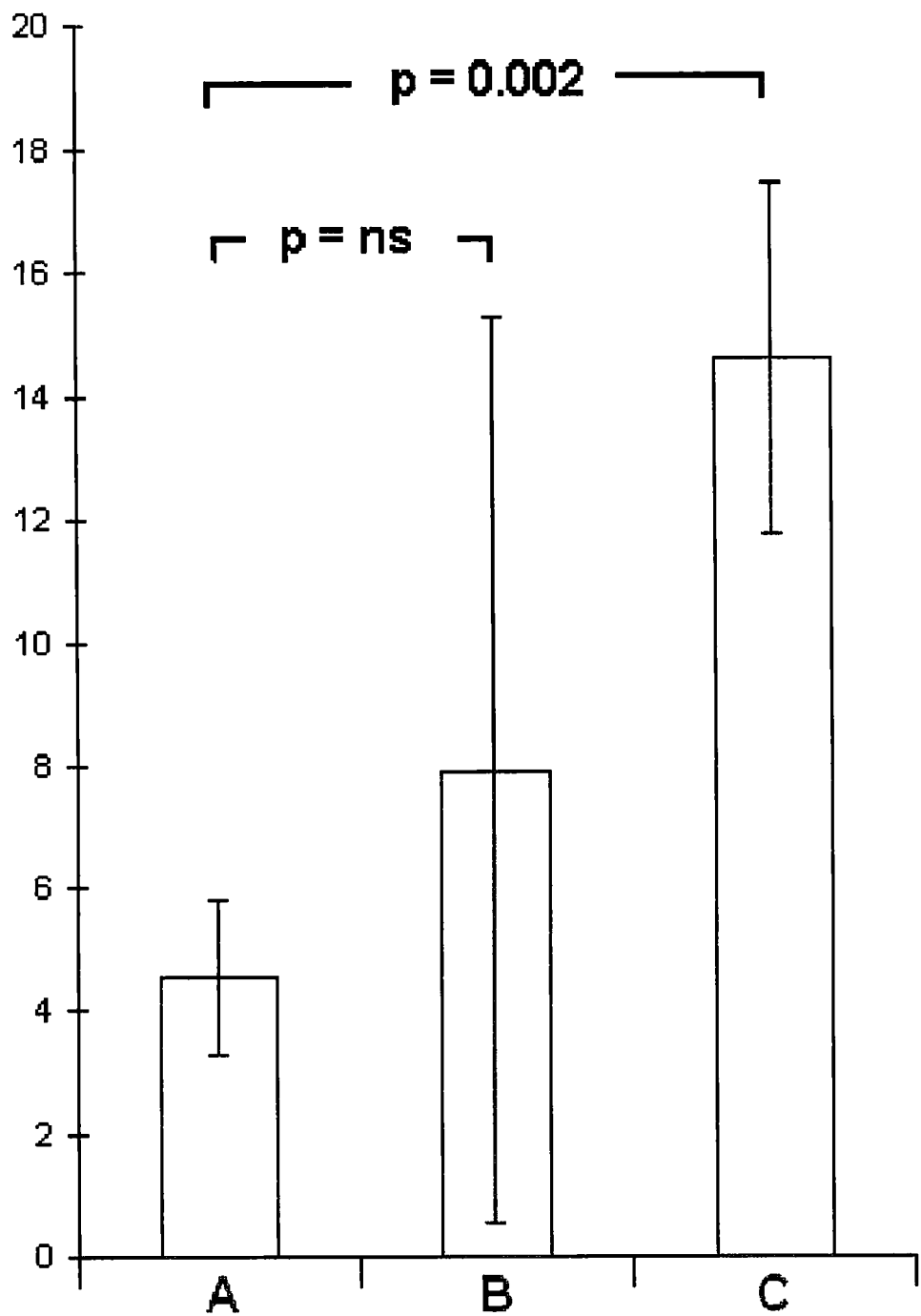
FIG. 13 compares the concentration of Paclitaxel (in µM) in the vessel wall of a pig iliac artery after 5 minutes of A) the direct infusion of 80 mg of Abraxane®; of B) the infusion of 80 mg of Abraxane® using a single balloon occlusion catheter; and of C) 25 mg of Abraxane® using the double balloon catheter; each followed by 15 minutes of washout. This is more thoroughly discussed in Example 1.

The double balloon catheter described herein was inserted into the iliofemoral artery of a pig while being monitored using fluoroscopic methods. The vessel was occluded by inflating the proximal balloon at which time a solution containing 25 milligrams of Abraxane® was infused. The distal balloon was inflated in a similar manner as the proximal balloon, thus forming the treatment window. After 5 minutes, the Abraxane® was washed from the treatment site by deflation of the balloons. The vessel was then allowed to wash out with circulating blood for 15 minutes. The concentration of Paclitaxel absorbed by the vessel wall was then determined. For comparison, a solution containing 80 milligrams Abraxane® was infused into the iliac artery of a pig using a direct infusion catheter and a single balloon occlusion catheter. Again, the concentration of Paclitaxel absorbed by the vessel wall was determined after 15 minutes of wash out. As exemplified graphically in FIG. 13, the concentration of Paclitaxel (microMolar) which was absorbed after 5 minutes of treatment using the double balloon catheter 10 (C) is substantially greater than that of the direct infusion catheter (A) and the single balloon occlusion catheter (B). The double balloon catheter 10 resulted in a Paclitaxel vascular tissue concentration of 15 microMolar using only 25 milligrams of Abraxane®. In contrast, using the direct infusion catheter with 80 milligrams of Abraxane® resulted in a Paclitaxel vascular tissue concentration of 6 microMolar.

Example 2

Homogeneity Determination

Also included as an embodiment of the present disclosure is an in vitro method for determining homogeneity of drug delivery. The method comprises the steps of a) placing a tubular member having a known length comprising a liquid of viscosity similar to the viscosity of blood in the path length of an optical sensor, b) delivering a dye of known concentration to the tubular member, and c) determining the concentration of dye along a length of the tubular member.

Two catheter configurations as shown in FIGS. 10 and 11, respectively, were studied to determine homogeneity of the therapeutic agent infusion upon delivery. An optical sensor was first calibrated using a series of FD&C Blue 31 dye samples of various known concentrations. A 6 mm diameter glass tube was used to simulate a blood vessel. The glass tube was mounted in the path of the optical sensor and placed in line with a peristaltic pump which circulated a solution having a viscosity matching that of blood (but optically clear) through the tube. Using each catheter as shown in FIGS. 10 and 11, 20 milliliters of dye solution was infused into the glass tube and the relative concentration of dye along the treatment window was measured. The results are discussed below.

For the catheter shown in FIG. 10, the infusion of 20 milliliters dye solution resulted in a mean drop of 1.64% from the original concentration of the infusate along a 25 centimeter path (Table 1).

TABLE 1

20 milliliters Infusion Relative Concentration

| Distance (cm) | Max Drop (%) | Mean Drop (%) | St. Dev. (%) |
|---|---|---|---|
| 0 | 4.88 | 3.26 | 1.92 |
| 5 | 4.14 | 2.14 | 1.89 |
| 10 | 1.90 | 1.14 | 1.01 |
| 15 | 2.29 | 0.76 | 1.32 |
| 20 | 3.02 | 1.26 | 1.57 |
| 25 | 3.76 | 1.64 | 1.85 |

For the catheter shown in FIG. 11, the infusion of 20 milliliters of dye solution resulted in a mean drop of 6.67% from the original concentration of the infusate along a 25 centimeter path (Table 2).

TABLE 2

20 milliliter Infusion Relative Concentration

| Distance (cm) | Max Drop (%) | Mean Drop (%) | St. Dev. (%) |
|---|---|---|---|
| 0 | 3.41 | 1.14 | 1.97 |
| 5 | 2.67 | 1.27 | 1.22 |
| 10 | 0.38 | 0.13 | 0.22 |
| 15 | 4.51 | 3.90 | 0.78 |
| 20 | 5.25 | 5.12 | 0.22 |
| 25 | 7.04 | 6.67 | 0.61 |

In a further study, 30 and 40 milliliters of dye solution was infused using the catheter shown in FIG. 11, and the relative concentration of dye along the 25 centimeter treatment window was measured. The maximum drop in concentration for 30 and 40 milliliters of dye solution was only 4.26% and 3.13%, respectively.

While the present disclosure has been disclosed with reference to certain embodiments, numerous modifications, alterations, and changes to the described embodiments are possible without departing from the sphere and scope of the present disclosure, as defined in the appended claims. Accordingly, it is intended that the present disclosure not be limited to the described embodiments, but that it has the full scope defined by the language of the following claims, and equivalents thereof.

We claim:

1. A method for site-specific delivery of a therapeutic agent to a blood vessel of a patient comprising the steps of:
   inflating first and second balloons of a catheter to define a treatment window between the first and second balloons;
   maintaining a fluid within the treatment window;
   selectively opening a closed drain passage that extends through the catheter to allow the fluid within the treatment window to be displaced from the treatment window and into the catheter through a leak aperture defined within a shaft of the catheter;
   delivering a therapeutic agent to the treatment window to displace the fluid from within the treatment window; and
   upon opening the drain passage, displacing the fluid through the drain passage by moving the fluid from the leak aperture to an opening defined in a distal end of the catheter that is positioned distally of the first and second balloons.

2. The method of claim 1 further comprising the step of delivering the therapeutic agent through the catheter to the treatment window.

3. The method of claim 1 wherein the step of inflating the first and second balloons includes inflating the first and second balloons to conform to an inner surface of a blood vessel to inhibit the flow of blood through the blood vessel.

4. The method of claim 1 further comprising the step of supporting at least one marker on the catheter.

5. The method of claim 4 further comprising the step of positioning the at least one marker adjacent at least one of the first and second balloons.

6. The method of claim 1 further comprising the step of changing a length of the treatment window.

7. The method of claim 6 further comprising the steps of:
   supporting the first balloon on an inner shaft of the catheter;
   supporting the second balloon on an outer shaft of the catheter; and selectively moving at least one of the inner shaft and the outer shaft relative to the other shaft to change the length of the treatment window.

8. A method for site-specific delivery of a therapeutic agent to a blood vessel of a patient comprising the steps of:
   inflating first and second balloons of a catheter to define a treatment window between the first and second balloons;
   maintaining a fluid within the treatment window;
   selectively opening a leak aperture defined within the catheter to allow the fluid within the treatment window to be displaced from the treatment window and into a drain passage that extends through the catheter;
   delivering a therapeutic agent to the treatment window to displace the fluid from within the treatment window; and
   positioning a guidewire within the catheter to block the leak aperture and prevent displacement of the fluid from the treatment window.

9. The method of claim 8 further comprising the step of selectively moving the guidewire to uncover the leak aperture and permit displacement of the fluid from the treatment window.

10. A method of site-specific delivery of a therapeutic agent to a blood vessel of a patient comprising:
    inserting a catheter into the vessel, the catheter supporting a proximal balloon and a distal balloon and defining a plurality of apertures;
    inflating the proximal balloon to substantially restrict blood flow through the vessel;
    inflating the distal balloon to form a treatment window between the proximal balloon and the distal balloon;
    positioning a guidewire within the catheter to block a distal leak aperture defined within the catheter;
    moving the guidewire to enable fluid within the treatment window to be displaced from the treatment window through the distal leak aperture and distally through a distal end of the catheter; and
    delivering the therapeutic agent through at least one of the plurality of apertures to displace the fluid disposed within the treatment window through the distal leak aperture to provide a substantially homogenous concentration of therapeutic agent within the treatment window.

11. The method of claim 10, wherein an amount of the therapeutic agent delivered to the treatment window is sufficient to substantially fill the treatment window.

12. The method of claim 10, wherein the therapeutic agent is selected from the group consisting of antiproliferative, anti-inflammatory, antineoplastic, antiplatelet, anticoagulant, antifibrin, antithrombin, antimitotic, antibiotic, and antioxidant substances.

13. The method of claim 10, wherein the therapeutic agent is paclitaxel.

14. The method of claim 10, wherein the distal balloon is inflated to form the treatment window prior to the step of delivering the therapeutic agent through the at least one of the plurality of apertures.

15. The method of claim 10 further comprising the step of supporting at least one marker on the catheter.

16. The method of claim 15 further comprising the step of positioning the at least one marker adjacent at least one of the proximal balloon and the distal balloon.

17. The method of claim 10 further comprising the step of changing a length of the treatment window.

\* \* \* \* \*